US00PP34383P3

(12) United States Plant Patent
Schoone

(10) Patent No.: US PP34,383 P3
(45) Date of Patent: Jun. 28, 2022

(54) ***PHALAENOPSIS* PLANT NAMED 'SPEECHLESS ELEGANCE'**

(50) Latin Name: *Phalaenopsis hybrida*
Varietal Denomination: Speechless Elegance

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 39 days.

(21) Appl. No.: 17/339,967

(22) Filed: Jun. 5, 2021

(65) Prior Publication Data

US 2021/0385993 P1 Dec. 9, 2021

Related U.S. Application Data

(60) Provisional application No. 62/705,003, filed on Jun. 6, 2020.

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
CPC ... A01H 5/02; A01H 5/00; A01H 5/08; A01H 6/62
See application file for complete search history.

*Primary Examiner* — June Hwu
(74) *Attorney, Agent, or Firm* — C. Anne Whealy

(57) ABSTRACT

A new and distinct cultivar of *Phalaenopsis* plant named 'Speechless Elegance', characterized by upright plant habit; moderately vigorous to vigorous growth habit; strong flowering stems; strong leaves; freely flowering habit with typically two inflorescences per plant, each inflorescence with numerous flowers; white-colored flowers that are densely covered with variable dark purplish red-colored blotches and spots; and good postproduction longevity.

2 Drawing Sheets

Figure 1:
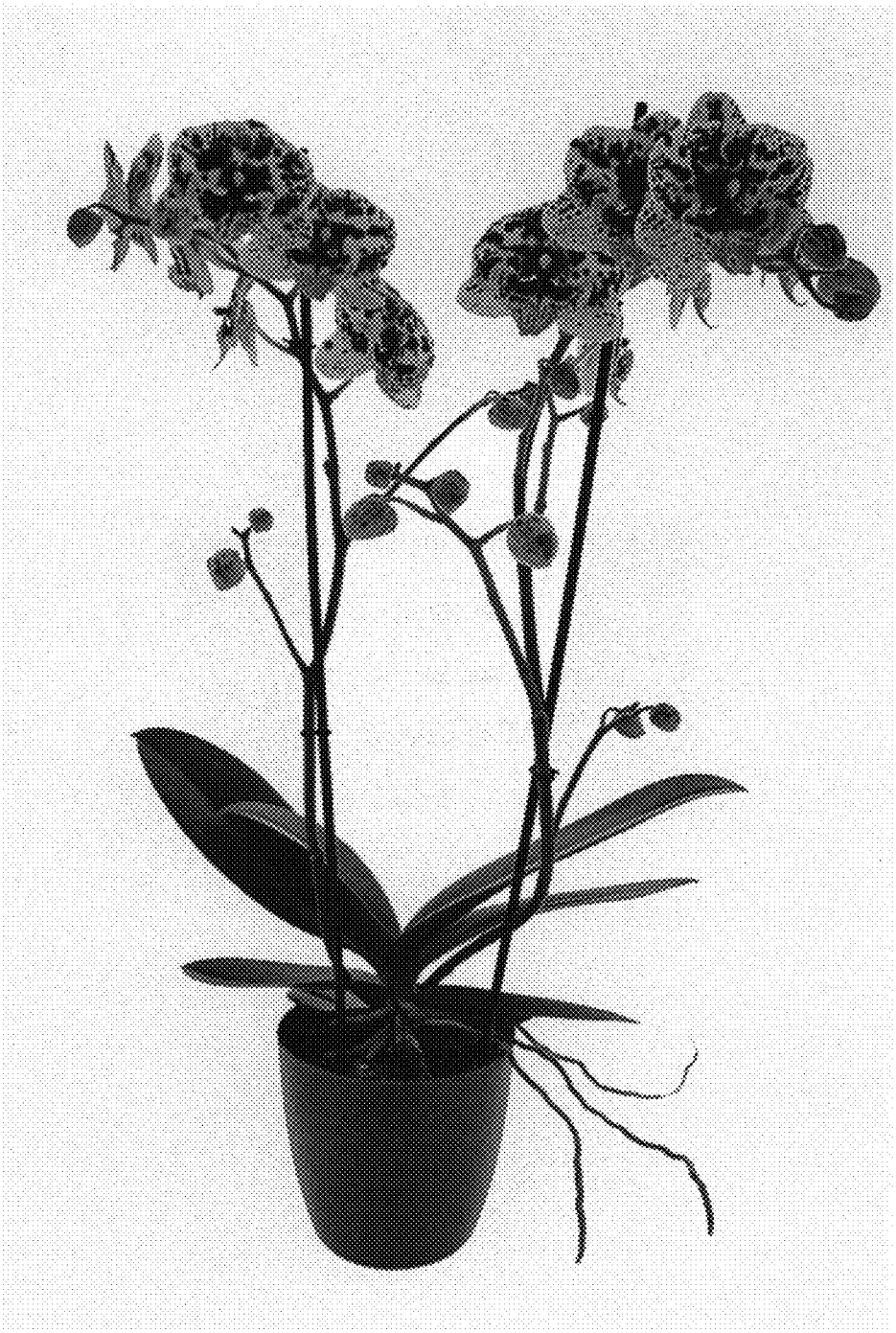

Botanical designation: *Phalaenopsis hybrida.*
Cultivar denomination: 'SPEECHLESS ELEGANCE'.

CROSS-REFERENCED TO CLOSELY-RELATED APPLICATIONS

Title: Varieties of *Phalaenopsis* Plants
Inventor: René Schoone
Filed: Jun. 6, 2020
Ser. No. 62/705,003
Inventor and Applicant/Assignee hereby claims the benefit of this provisional U.S. Patent Application.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Floricultura B.V. of Heemskerk, The Netherlands on Sep. 17, 2020, application number 2020/2194. Foreign priority is not claimed to this European Community Plant Breeder's Rights application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'Speechless Elegance'.

The new *Phalaenopsis* plant is a product of a planned breeding program conducted by the Inventor in Nantou, Taiwan and Heemskerk, The Netherlands. The objective of the breeding program is to develop new fast-growing and freely flowering *Phalaenopsis* plants with good leaf shape and large flowers with unique and attractive patterns and coloration.

The new *Phalaenopsis* plant originated from a cross-pollination in January, 2011 in Nantou, Taiwan of *Phalaenopsis hybrida* 'Fuller's Goddess', not patented, as the female, or seed, parent with *Phalaenopsis hybrida* 'World Class' x 'Kungs Amar Dott "Big Lip"', not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in September, 2017.

Asexual reproduction of the new *Phalaenopsis* plant by in vitro meristem propagation in a controlled environment in Assendelft, The Netherlands since September, 2018 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Speechless Elegance'. These characteristics in combination distinguish 'Speechless Elegance' as a new and distinct *Phalaenopsis* plant:

1. Upright plant habit.
2. Moderately vigorous to vigorous growth habit.
3. Strong flowering stems.
4. Strong leaves.
5. Freely flowering habit with typically two inflorescences per plant, each inflorescence with numerous flowers.
6. Flowers with fused labella, typically referred to as a "big lip" type.
7. White-colored flowers that are densely covered with variable dark purplish red-colored blotches and spots.
8. Good postproduction longevity.

Plants of the new *Phalaenopsis* can be compared to plants of the female parent, 'Fuller's Goddess'. Plants of the new *Phalaenopsis* differ primarily from plants of 'Fuller's Goddess' in flower shape as flowers of plants of the new *Phalaenopsis* have imbricate petals whereas flower petals of plants of 'Fuller's Goddess' are not imbricate. In addition, the labellum lateral and central lobes are fused in plants of the new *Phalaenopsis* whereas the lateral and central lobes of the labellum of plants of 'Fuller's Goddess' are not fused.

Plants of the new *Phalaenopsis* can be compared to plants of the male parent, 'World Class' x 'Kungs Amar Dott "Big Lip"'. Plants of the new *Phalaenopsis* differ primarily from plants of 'World Class' x 'Kungs Amar Dott "Big Lip"' in flower shape as flowers of plants of the new *Phalaenopsis* have imbricate petals whereas flower petals of plants of 'World Class' x 'Kungs Amar Dott "Big Lip"' are not imbricate. In addition, flowers of plants of the new *Phalaenopsis* are densely covered with variable blotches and spots whereas flowers of plants of 'World Class' x 'Kungs Amar Dott "Big Lip"' do not have blotches and spots.

Plants of the new *Phalaenopsis* can be compared to plants of x *Doritaenopsis* 'Untold Stories', disclosed in U.S. Provisional Patent application Ser. No. 62/705,005 and in a U.S. Plant patent application Ser. No. 17/340,016 filed concurrently. In side-by-side comparisons, plants of the new *Phalaenopsis* differ primarily from plants of 'Untold Stories' in flower shape as flower petals of plants of the new *Phalaenopsis* are more overlapping than flower petals of plants of 'Untold Stories'. In addition, petal blotches and spots of plants of the new *Phalaenopsis* are more distinct and not as coalescing as petal blotches and spots of plants of 'Untold Stories'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Speechless Elegance' grown in a container.

Figure 2:
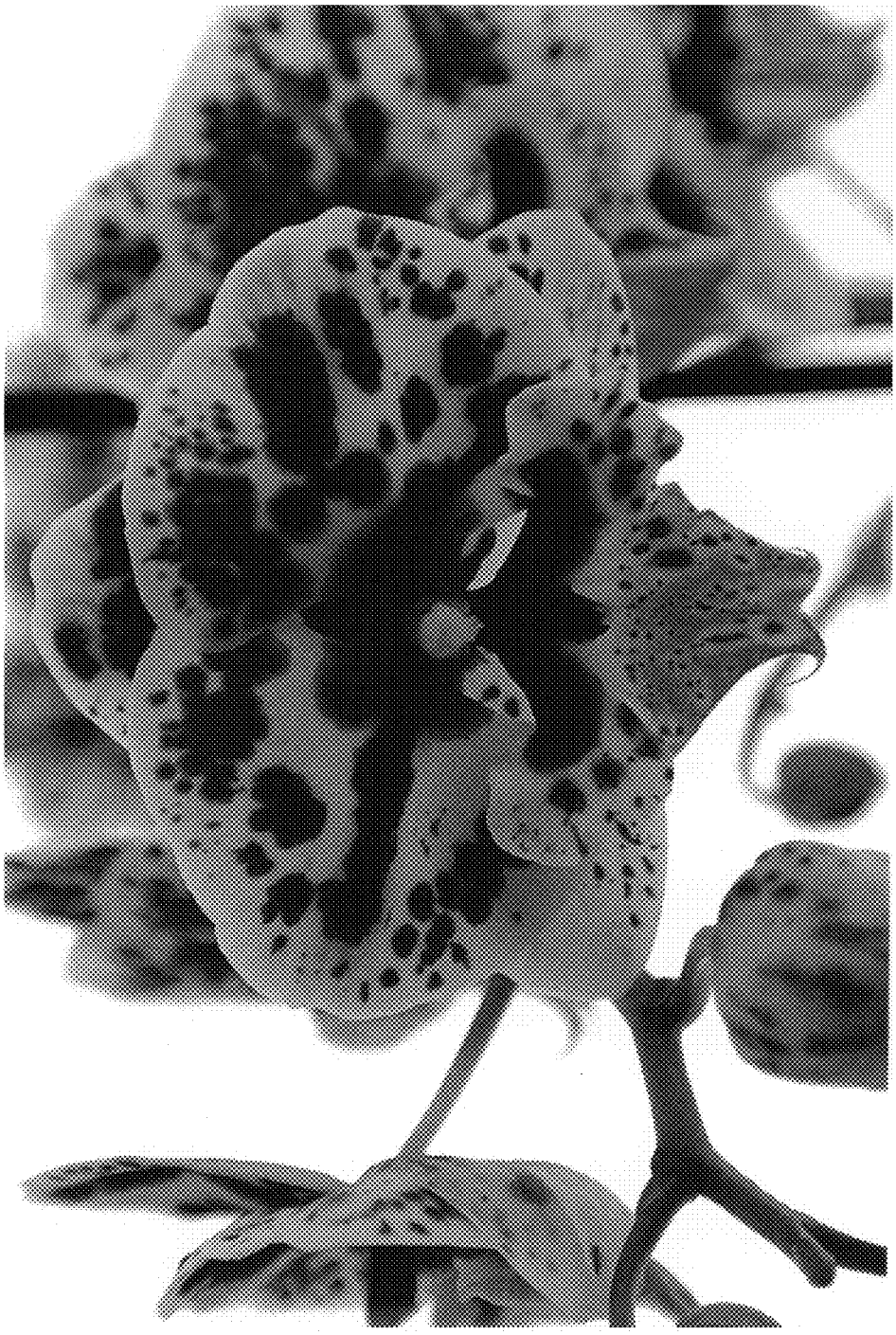

The photograph on the second sheet (FIG. 2) is a close-up view of a typical flower of 'Speechless Elegance'.

DETAILED BOTANICAL DESCRIPTION

The aforementioned photographs and following observations and measurements describe plants grown during the early winter in 10.5-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the 18 months of production, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Speechless Elegance'.

Parentage:

*Female parent.*—*Phalaenopsis hybrida* 'Fuller's Goddess', not patented.

*Male parent.*—*Phalaenopsis hybrida* 'World Class' x 'Kungs Amar Dott "Big Lip"', not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thick, fibrous; typically grey to green in color; actual color of the roots is dependent on substrate composition, water quality, fertilizer, substrate temperature and age of roots.

*Rooting habit.*—Low amount of branching; medium density.

Plant description:

*Plant form and growth habit.*—Herbaceous epiphyte; upright plant habit with typically two inflorescences per plant, each inflorescence with numerous flowers; monopodial; moderately vigorous to vigorous growth habit and moderate growth rate.

*Plant height, substrate level to top of foliar plane.*—About 19.2 cm.

*Plant height, substrate level to top of inflorescences.*—About 51.6 cm.

*Plant diameter or spread.*—About 31.6 cm.

Leaf description:

*Arrangement and quantity.*—Distichous, simple; sessile; about six leaves per plant.

*Length.*—About 22.4 cm.

*Width.*—About 7.4 cm.

*Aspect.*—Upright to outwardly arching.

*Shape*.—Oblanceolate to narrowly oblong; moderately carinate.

*Apex*.—Unequal acute.

*Base*.—Sheathing. Sheath length: About 1.8 cm. Sheath width: About 1.7 cm. Sheath color: Close to 143A to 143B; distal margin, close to between 137A and 143A.

*Margin*.—Entire; not undulate.

*Texture and luster, upper and lower surfaces*.—Smooth, glabrous; slightly to moderately glossy.

*Venation pattern*.—Camptodromous.

*Color*.—Developing leaves, upper surface: Close to between NN137A and 139A. Developing leaves, lower surface: Close to 146A. Fully expanded leaves, upper surface: Close to between 137A and NN137B; venation, close to NN137A. Fully expanded leaves, lower surface: Close to 146A to 146B; venation, close to NN137A.

Inflorescence description:

*Appearance and flowering habit*.—Showy zygomorphic flowers arranged on axillary branched racemes; typically two inflorescences per plant; each inflorescence with about 15 flowers; flowers face outwardly on arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity*.—Long flowering period, individual flowers maintain good substance for about four weeks on the plant; flowers not persistent.

*Inflorescence length* (*lowermost flower to inflorescence apex*).—About 30.3 cm.

*Inflorescence width*.—About 21.4 cm.

*Flower buds*.—Height: About 2.1 cm. Diameter: About 1.7 cm by 1.8 cm. Shape: Broadly ovate. Color: Close to 145C; towards the base, close to 150B; variably dotted, close to N79A to N79B.

*Flower size*.—About 7.7 cm (vertical) by 7.6 cm (horizontal).

*Flower depth*.—About 2.7 cm.

*Petals, quantity and arrangement*.—Three, two lateral petals and one center petal transformed into a labellum.

*Lateral petals*.—Length: About 3.8 cm. Width: About 4.9 cm. Shape: Lunate to reniform; slightly convex. Apex: Broad, shallowly retuse to rounded. Margin: Entire. Texture and luster, upper and lower surfaces: Smooth, glabrous, velvety; matte. Color: When opening, upper surface: Close to NN155D with variable blotches and spots, close to 59A, 187B and 187C; at the base (at column connection), close to 187B. When opening, lower surface: Close to NN155B to NN155C with variable blotches and spots, close to 59A, 187B and 187C; at the base (at column connection), close to 187B. Fully opened, upper surface: Close to NN155D with variable blotches and spots, close to 59A, N79C and 187B; at the base (at column connection), close to 187B. Fully opened, lower surface: Close to NN155D with variable blotches and spots, close to N79B, N79C and N186D; at the base (at column connection), close to N79C.

*Labella*.—Appearance: Lateral and central lobes fused towards the base into a single lobe, typically referred to as a "big lip" type. Length, lateral lobes: About 2.2 cm. Width, lateral lobes: About 1.7 cm. Length, central lobe: About 3.5 cm. Width, central lobe: About 2.6 cm. Shape, lateral and central lobes: Overall, roughly deltoid to reniform. Shape, lateral lobes: Broadly obovate-falcate. Shape, central lobe: Rhomboidal. Apex, lateral lobes: Obtuse. Apex, central lobe: Emarginate with two narrow and strongly recurved cirrose tips, about 3 mm in length and about 1 mm in width. Margins, lateral and central lobes: Entire; slightly undulate. Texture and luster, upper and lower surfaces: Smooth, glabrous, moderately velvety; matte. Callosities: Located at the base of the labellum and attachment point of the lateral petals; about 4 mm in length, about 3.5 mm in width and about 6 mm in height. Color, lateral and central lobes: When opening, upper surface: Close to NN155D; densely covered with variable blotches, close to N78B and N78C, and densely covered with variable spots, close to 59A, 187B and 187C; towards the upper margin, close to 187B; at the base (at column connection), close to 187B; callosities, close to 187B. When opening, lower surface: Close to 155C; towards the margins, close to NN155D; densely covered with variable blotches, close to N78B and N78C, and densely covered with variable spots, close to N79B and N79C; towards the upper margin, close to between N77A and N77B; at the base (at column connection), close to between N77A and N77B. Fully opened, upper surface: Close to NN155D; densely covered with variable blotches, close to N78B and N78C, and densely covered with variable spots, close to N79B and N79C; towards the upper margin, close to N79B, N186C, 187C and 187D; at the base (at column connection), close to N79B, N186C, 187C and 187D; callosities, close to 187B. Fully opened, lower surface: Close to NN155D; densely covered with variable blotches, close to N78B and N78C, and moderately covered with variable spots, close to N79C; towards the upper margin, close to N79B and N79C; at the base (at column connection), close to N79B and N79C.

*Sepals*.—Quantity and arrangement: Three, one upper dorsal sepal and two lower lateral sepals. Length, dorsal sepal: About 4.2 cm. Width, dorsal sepal: About 3.3 cm. Length, lateral sepals: About 4.2 cm. Width, lateral sepals: About 3 cm. Shape, dorsal sepal: Broadly elliptic to broadly ovate. Shape, lateral sepals: Broadly ovate. Apex, dorsal sepal: Broadly emarginate. Apex, lateral sepals: Bluntly acute. Base, dorsal and lateral sepals: Truncate. Margin, dorsal and lateral sepals: Entire. Texture and luster, dorsal and lateral sepals, upper and lower surfaces: Smooth, glabrous, velvety; matte. Color, dorsal sepal: When opening, upper surface: Close to NN155D; towards the margins and apex, close to 157B; large distal blotch, close to N78C; densely covered with variable spots, close to 187A and 187B; at the base (at column connection), close to 187A. When opening, lower surface: Close to between 150D and 157A; large distal blotch, close to NN74D; densely covered with variable spots, close to N79A and N79B; at the base (at column connection), close to N79A and N79B. Fully opened, upper surface: Close to NN155D; large distal blotch, close to N78D to lighter than N78D; densely covered with variable blotches and spots, close to N79A, N79B and 187B; at the base (at column connection), close to 187B. Fully opened, lower surface: Close to NN155D; large distal blotch, close to 77B to 77C; densely covered with variable blotches and spots, close to N79B and N79C; at the base (at column connection), close to N79B. Color, lateral sepals: When opening, lower surface: Close to NN155D; lower half, close to 150D; densely covered with variable spots, close to 187A to 187B; at the base (at column connection), close to 187A. When opening, lower surface: Close to 150D, 154C and 154D; densely covered with variable spots, close to N79B and 187B; at the base (at column connection), close to N79B. Fully opened, upper surface: Close to NN155D; densely covered with variable blotches and spots, close to N79C; at the base (at column connection), close to N79B. Fully opened, lower surface: Close to NN155B to NN155C; densely covered with variable blotches and spots, close to N78A, N78B and N79C; at the base (at column connection), close to N79C.

*Peduncles*.—Length: About 52.6 cm. Diameter: About 7 mm. Strength: Strong. Aspect: Upright to outwardly arching. Texture and luster: Smooth, glabrous; matte. Color: Close to 144A; proximally, close to 147A; fine dots, close to 146B.

*Pedicels*.—Length: About 4.4 cm. Diameter: About 3 mm. Strength: Moderately strong. Aspect: About 50° from peduncle axis. Texture and luster: Smooth, glabrous; matte. Color: Close to 147D; distally, close to between 157A and 196D and proximally, close to 197B to 197C.

*Reproductive organs*.—Androecium: Column length: About 8 mm. Column width: About 5.5 mm. Column color: Close to N79C; distally, close to N155A. Pollinia quantity: Two. Pollinia diameter (per two pollinia): About 2.5 mm. Pollinia color: Close to 23A. Gynoecium: Stigma length: About 2 mm. Stigma width: About 4 mm. Stigma shape: Reniform. Stigma color: Close to N155A with margins, close to N79C. Ovary length: About 8 mm. Ovary diameter: About 1 mm. Ovary color: Close to 145C. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate temperatures ranging from about 15° to about 40° C. and are suitable for USDA Hardiness Zones 10 to 12.

It is claimed:

1. A new and distinct *Phalaenopsis* plant named 'Speechless Elegance' as illustrated and described.

* * * * *